United States Patent [19]
Suh et al.

[11] Patent Number: 5,989,270
[45] Date of Patent: Nov. 23, 1999

[54] NOSE SHAPE ADJUSTING INSTRUMENT

[75] Inventors: Jeong-joo Suh, Seoul; Hyoung-sob Shim, Tangjin-kun, Chungcheong-namdo, both of Rep. of Korea

[73] Assignee: Eunsung Development Co., Ltd., Seoul, Rep. of Korea

[21] Appl. No.: 09/227,474

[22] Filed: Jan. 8, 1999

[30] Foreign Application Priority Data

Apr. 15, 1998 [KR] Rep. of Korea .......................... 98-5931
Oct. 2, 1998 [KR] Rep. of Korea ....................... 98-19074

[51] Int. Cl.$^6$ .................................................. A61B 17/08
[52] U.S. Cl. ............................................................ 606/157
[58] Field of Search ..................... 606/162, 157; 119/866

[56] References Cited

U.S. PATENT DOCUMENTS 4,175,306  11/1979  Bigelow et al. ........................... 24/253
4,369,783  1/1983  Hiller et al. .............................. 128/260

*Primary Examiner*—Michael Buiz
*Attorney, Agent, or Firm*—Baker & Botts, L.L.P.

[57] ABSTRACT

Disclosed is a nose shape adjusting instrument which comprises an inverted U-shaped body conforming to the general shape of a nose, the body having compressing portions on an end opposite from the closed end thereof; a plurality of attachment plates for attaching on the compressing portions; a tightening bolt inserted through holes formed on the compressing portions for adjusting the distance between the compressing portions; and a tightening nut for pairing with the tightening bolt.

5 Claims, 7 Drawing Sheets

NOSE SHAPE ADJUSTING INSTRUMENT

BACKGROUND OF THE INVENTION (a) Field of the Invention

The present invention relates to a nose shape adjusting instrument, more particularly to a nose shape adjusting instrument which is capable of elevating a nose tip by compressing wings of a nose.

(b) Description of the Related Art

It is generally considered that a high-ridged and narrow nose is more beautiful than a low and broad nose. This notion has led to various methods for adjusting one's shape of nose. The most commonly known methods for adjusting the shape of a nose include such widely tried method as clamping of a nose by a clothespin and more drastic measure of a plastic surgery. Nowadays, the number of people opting for the surgery is ever more increasing.

However, the cost of the plastic surgery is very high, and many side effects of the plastic surgery have been continuously reported. Besides, before the surgery is performed, the people concerned, especially the young ones, usually undergo a very stressful experience due to their sensitivity regarding their nose, which could have serious repercussions on the personality of the involved ones.

Meanwhile, the use of a clothespin tends to compress the nose too severely. Therefore, the pain is great and, scars are sometimes inflicted upon, especially when the period of time the user has his or her nose clamped is prolonged.

SUMMARY OF THE INVENTION

The present invention has been made in an effort to address the problems of the prior art. The present invention provides a nose shape adjusting instrument for adjusting the shape of a nose, which is usable any period of time, while not disrupting the user's work or sleep and causing no harm to the skin.

To achieve the above object, a nose shape adjusting instrument of the present invention includes an inverted U-shaped body conforming to the general shape of a nose, having compressing portions on an end opposite from the closed end of the body; a plurality of attachment plates for attaching on the compressing portions; a tightening bolt inserted through holes formed on the compressing portions for adjusting the distance between the compressing portions; and a tightening nut for pairing with the tightening bolt.

BRIEF DESCRIPTION OF THE DRAWINGS

A more complete appreciation of the invention will be readily apparent as the same becomes better understood by reference to the following detailed description when considered in conjunction with the accompanying drawings, wherein.

DETAILED DESCRIPTION OF THE INVENTION

Reference will now be made in detail to the preferred embodiments of the present invention, examples of which are illustrated in the accompanying drawings.

Figure 1:
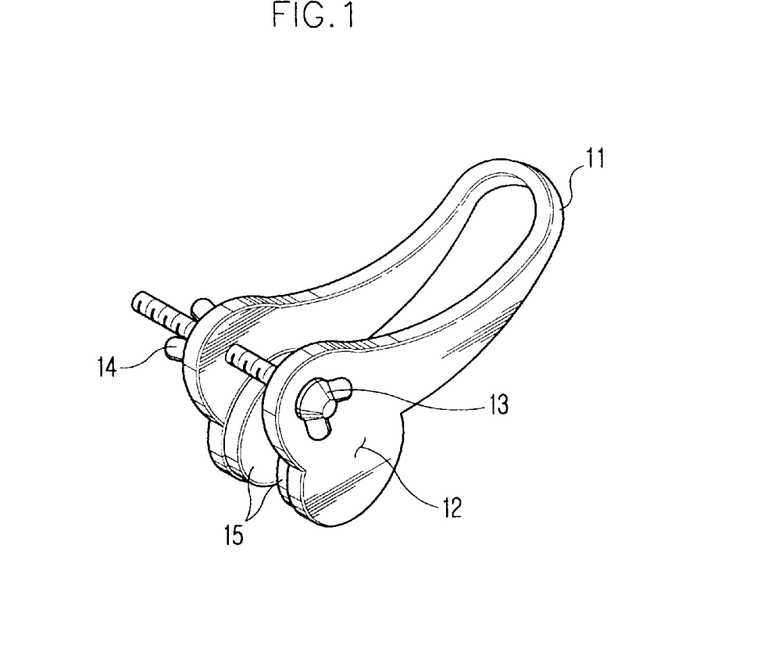
FIG. 1 is a perspective view of a nose shape adjusting instrument of a first preferred embodiment of the present invention.

FIGS. 1 through 6 relate to a nose shape adjusting instrument according to a first preferred embodiment of the present invention. As shown in FIG. 1, the nose shape adjusting instrument 10 has an inverted U-shaped body to conform to the general shape of a nose. The body of the instrument, where nose of a wearer is to be engaged, is divided into two portions: a tension portion 11 and a compressing portion 12. The compressing portion 12 corresponds to low end portions of the inverted U-shape and the tension portion corresponds to remaining portion of the inverted U-shape. The tension portion 11 forms a gentle curve conforming to the shape of a nose along the ridge. The length of the nose shape adjusting instrument is determined such that an uppermost end of the tension portion is placed between the eyes of the wearer. The compressing portion 12 is two substantially round plates facing each other flared from the tension portion for engaging the tip and wings of a nose. (The compressing portion is also referred to as compressing plates hereinafter under the same numeral reference 12.) An aperture 12b is formed on each of the compressing plates 12. Below the aperture are formed several protrusions 12a protruding to a center of the inverted U-shaped body.

A tightening bolt 13 is inserted through the holes formed on the compressing plates 12 for adjusting a distance between the two compressing plates 12 and, a tightening nut 14 is provided to pair with the tightening bolt 13. Head of the tightening bolt 13 and the tightening nut 14 are placed on the outer circumference of the compressing plates 13 such that, when the tightening nut 14 is tightened on the bolt 13, the two facing compressing plates 12 are forced to narrow the distance therebetween.

Figure 2:
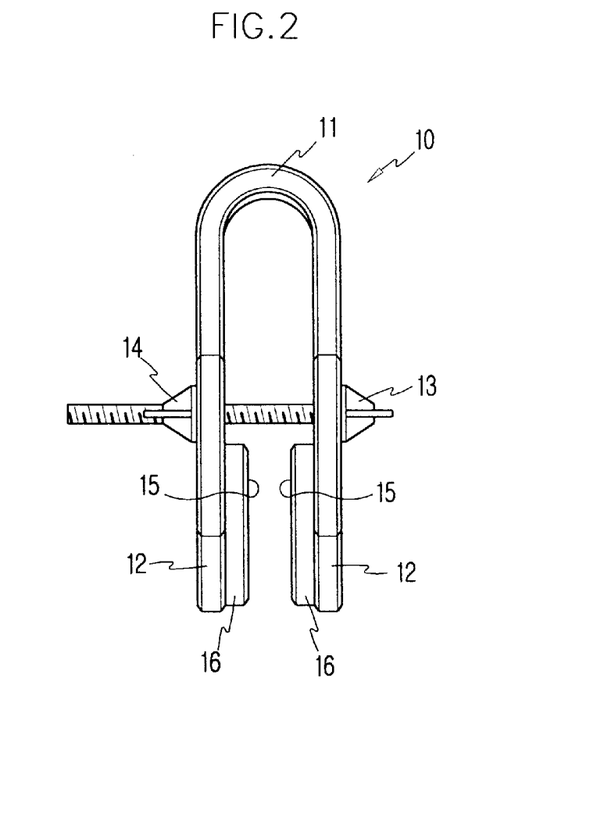
FIG. 2 is a top view of the nose shape adjusting instrument shown in FIG. 1.
Figure 3:
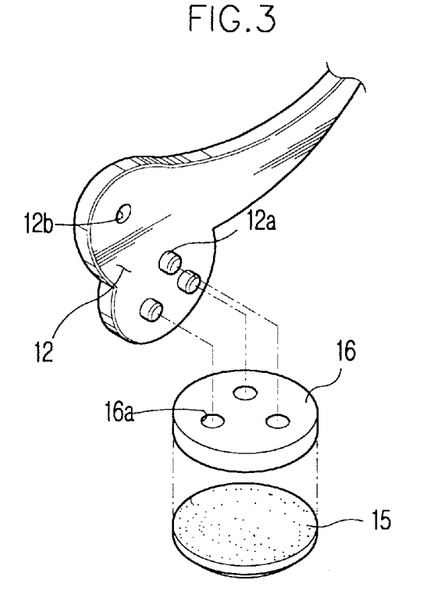
FIG. 3 is a schematic view of a compressing portion shown in FIG. 1.

Referring to FIGS. 2 and 3, the nose shape adjusting instrument 10 further includes a plurality of attachment plates 16 for attaching on the compressing plates 12. The attachment plates 16 are circular plates through which several apertures 16a are formed to receive the corresponding protrusions 12a formed on the compressing portion 12. A plurality of rubber plates 15 are fixed on the attachment plates 16.

Figure 4:
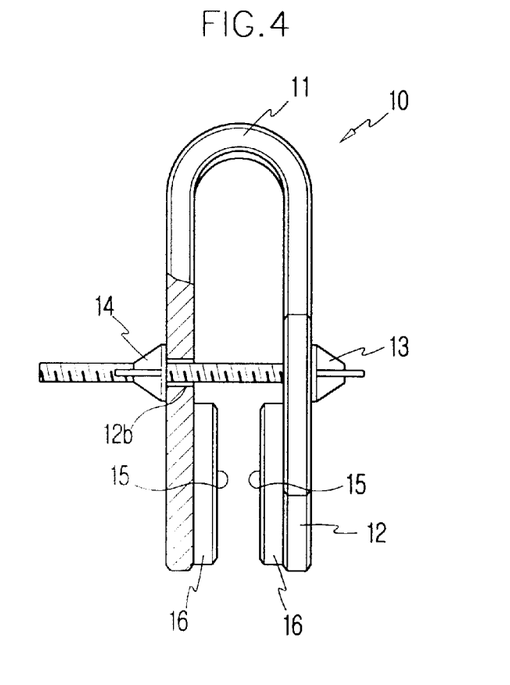
FIG. 4 is a top view of the nose shape adjusting instrument of FIG. 1 in a state where a bolt and a nut thereof are tightened.
Figure 5:
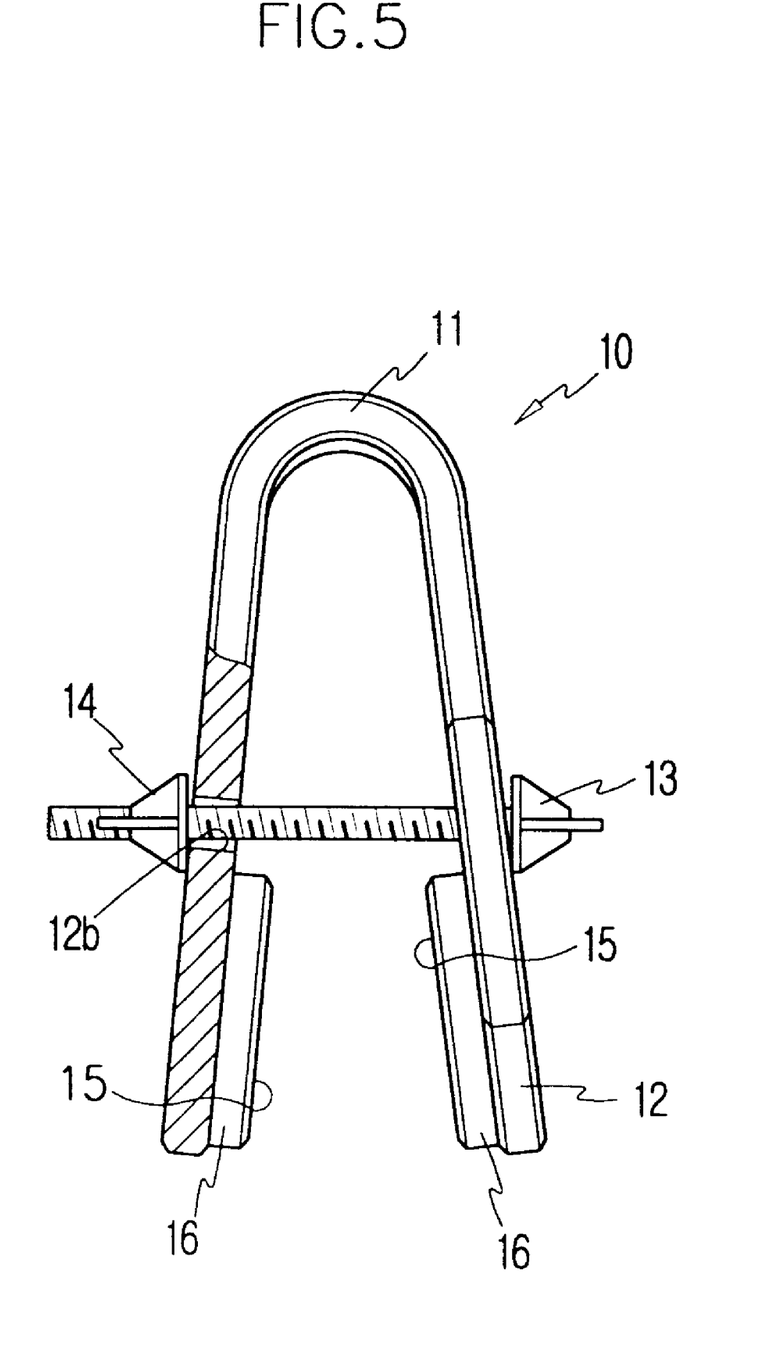
FIG. 5 is the nose shape adjusting instrument of FIG. 4 in a state where the bolt and the nut are not tightened.
Figure 6:
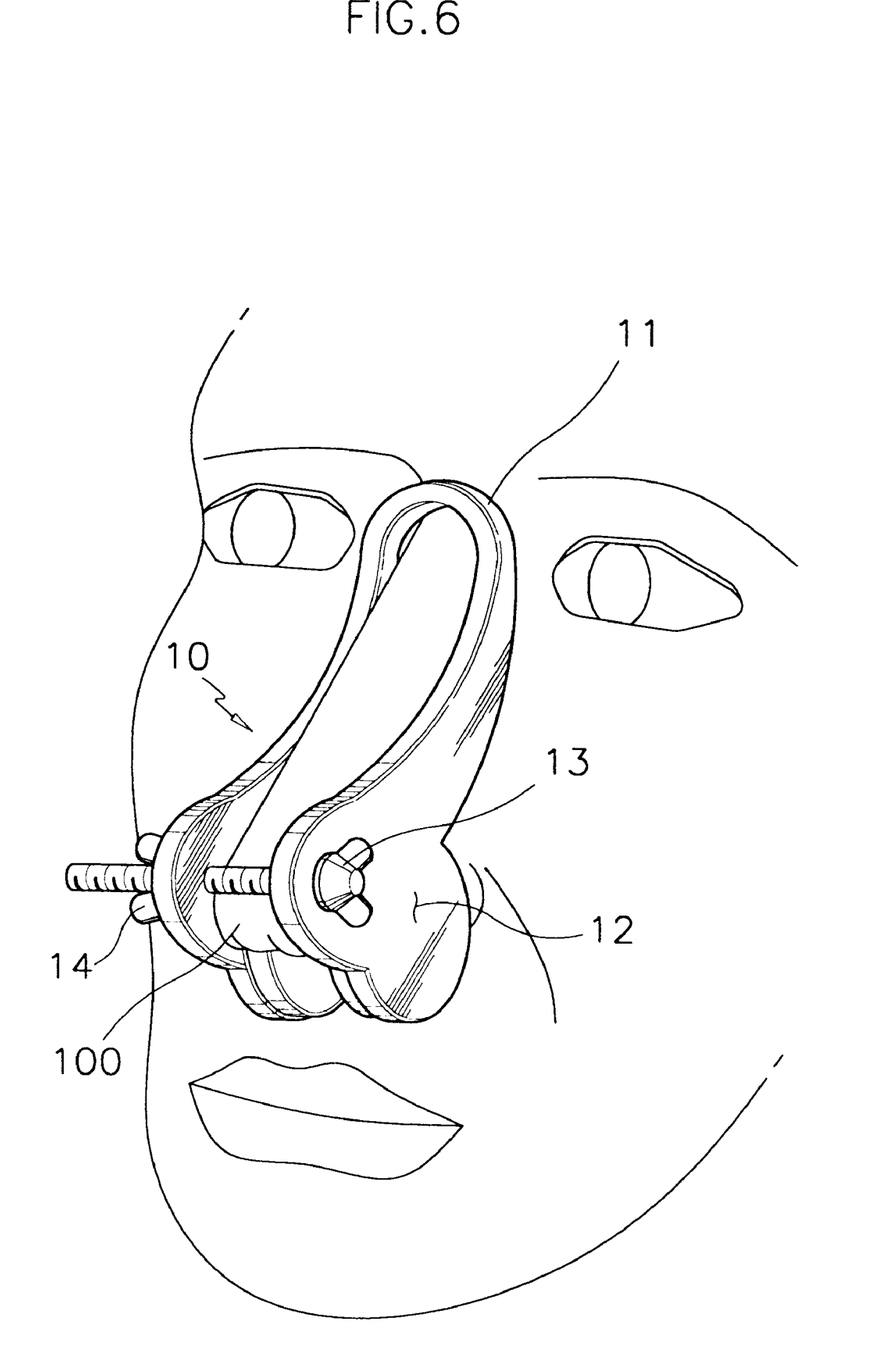
FIG. 6 shows the nose shape adjusting instrument of FIG. 1 in a state where it is worn on a face.

In order to make the hand tightening of the tightening bolt 13 and the nut 14 is easily performed, a wing bolt and a wing nut are used. The user can adjust the degree of compression on the wings of the nose by changing the degree of tightening of the bolt and the nut as shown in FIGS. 4 and 5 All components for the present invention are made of synthetic resins. FIG. 6 shows the invented instrument in a state where it is secured to the outer surface of a person's nose 100.

How the nose shape adjusting instrument of the first preferred embodiment is worn and operates is described hereinafter.

First, the user places the instrument in a middle of his or her face such that his or her nose on the nostril side is fitted between the rubber plates 15 and that the upper most end of the tension portion 11 is mounted on the ridge of the nose between the eyes. Then, the user tightens the tightening nut 14 on the bolt 13 to a degree appropriate and comfortable to the user.

The tightening of the nut 14 makes the compressing plates 12 reduce the gap therebetween, and therefore, the wings of the nose interposed between the rubber plates 15 are compressed and the nose tip is elevated.

Since soft rubber plates 15 are provided at the portion of the invented instrument directly contacting the skin of the user, the user is not subjected to the danger of harming the skin. Also, by adjusting the degree of compression on the nose, the user's breathing process is not interfered with. Therefore, the user can safely adjust the shape of his or her nose for any duration of time regardless of day and night.

Figure 7:
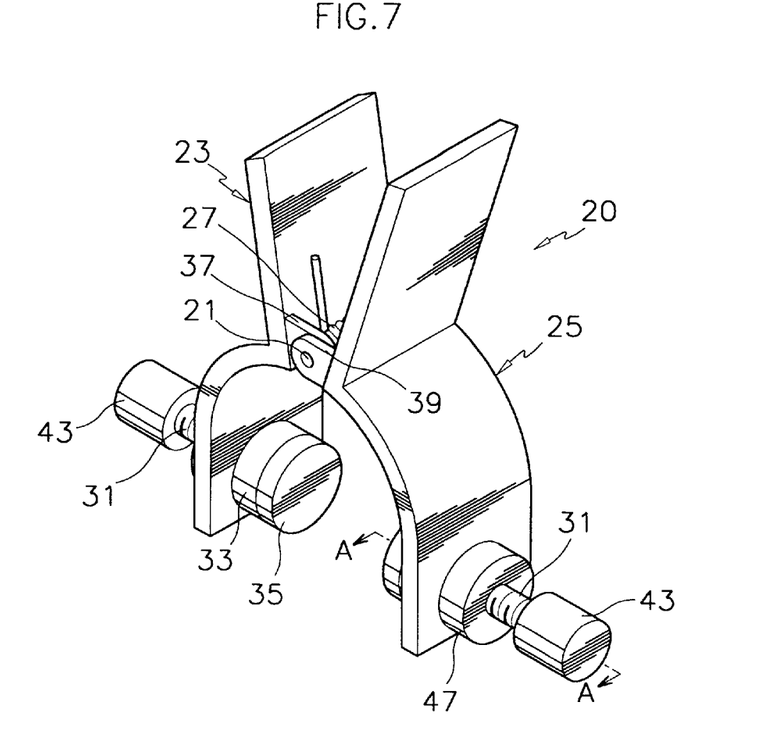
FIG. 7 is a perspective view of a nose shape adjusting instrument of a second preferred embodiment of the present invention.
Figure 8:
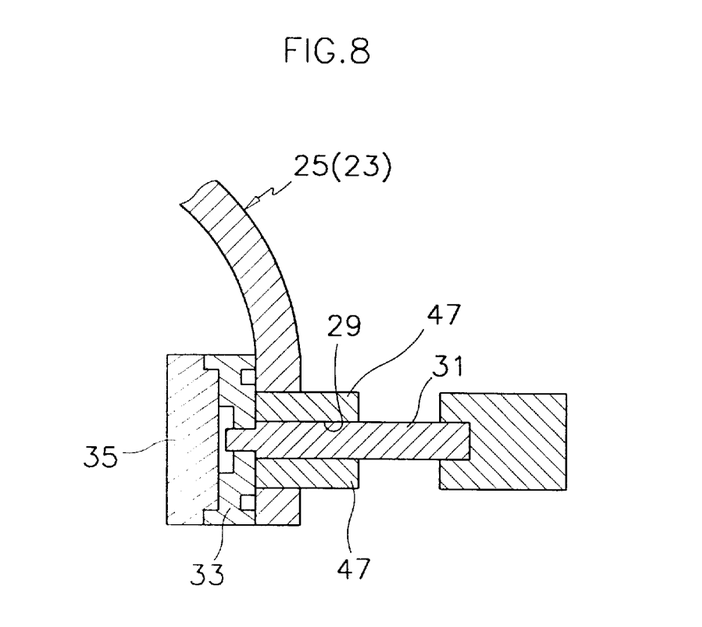
FIG. 8 is a partial sectional view of the nose shape adjusting instrument shown in FIG. 7.
Figure 9:
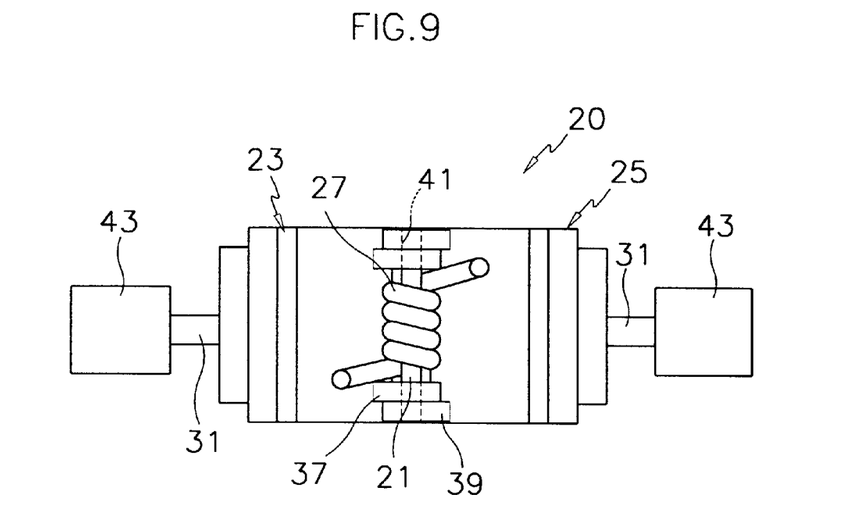
FIG. 9 is a top view of the nose shape adjusting instrument shown in FIG. 7.

Next, FIGS. 7 through 9 show a nose shape adjustment instrument s according to a second preferred embodiment of the present invention. Saving the written-below, the instrument operates identically to the nose shape adjusting instrument of the first embodiment.

The nose shape adjusting instrument according to a second preferred embodiment as shown in FIG. 7 includes a first body 23 and a second body 25 which are symmetrical and rotatably connected to each other around a center thereof by a hinge mechanism. Centering on the hinge mechanism provided between the first and the second body 23 and 25, the shape of the first and the second body is decided such that the upper portions of the first and second body substantially form a substantially V-shape, and the lower portions of the two bodies form an arch. That is, the first body 23 is bent around a center thereof and, the upper portion is a rectangular plate and the lower portion is a curved plate, the curvature substantially equaling to a half arch form. The width of the first body 23 is determined to be a little larger than the general length of wings of people's nose.

A hinge axis 21 as shown in FIG. 9 is provided between the first and the second body 23 and 25 around the center thereof where the semi-arch form begins. Ends of the hinge axis 21 are inserted through holes formed on protrusions 37 and 39, the protrusions 37 being formed on the first body 23 just above the semi-arch form and facing the second body 25 and, the protrusions 39 being formed on the second body 25 just above the semi-arch form and facing the first body 23.

Figure 10:
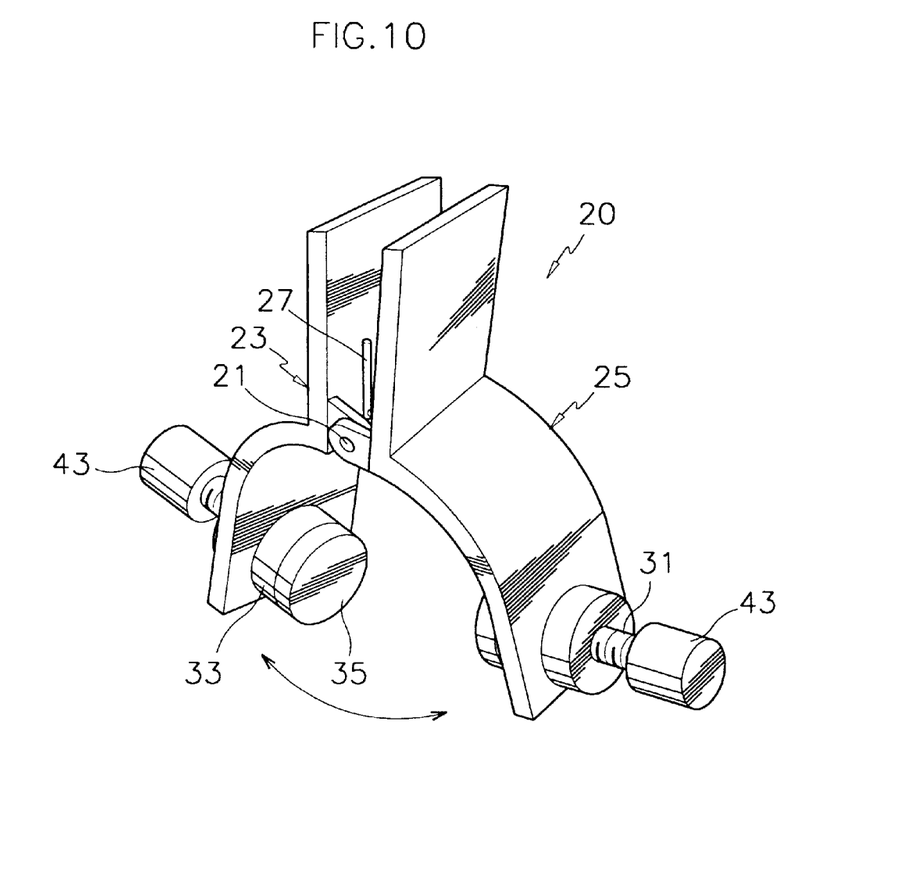
FIG. 10 is a perspective view of the nose shape adjusting instrument shown in FIG. 7 in a state where a bolt and a nut are not tightened.

Referring to FIGS. 7 and 9, an elastic member 27 is provided winding around the hinge axis 21, the ends of which extend to the opposite direction from each other such that the respective ends press the upper portions of the first and the second body. The elastic member 27 exerts a biasing force on the upper portions of the first and the second body to maintain the substantially V-shape formed by the upper portions of the first and the second body. By this configuration, when the upper portions of the first and second body are narrowed, that is, when the ends of the elastic member are pushed closer to each other, the lower portions of the first and the second body are rotated around the hinge axis 21, widening the gap between the lowest portions of the first and the second body as shown in FIG. 10.

In order to strengthen the body structures, a plurality of supporting members 47, cylinders with a hole in the center, are inserted through the lower portions of the first and the second body 23 and 25. The supporting members 47 can be either integrally formed or tightly fitted on the first and the second body.

A pair of adjusting bolt 31 and a pad support disc 33 is provided mounted on each of the first and the second body. The adjusting bolts 31 are placed on the outer circumference of the lower portions of the first and the second body and the supporting discs 33 are placed on the inner circumference of the arch made by the first and the second body. The adjusting bolts 31 are inserted through apertures 29 formed on the supporting members 47 which are fitted into the first and the second body. To receive the adjusting bolts 31, the wall of the hole 29 formed on the supporting members 47 has internal threads corresponding to the threads of the bolts 31.

In order for the user to easily drive the bolt 31, the shape of the head portion 43 of the adjusting bolt 31 placed on the outer circumference of the first and the second body is changed into a cylinder or a cubicle, etc. The adjusting bolts and nuts are provided to adjust the degree of compression on the nose interposed between the first body and the second body.

A plurality of circular contact plates 35 made of a resilient and soft material such as a silicon are attached to the supporting discs 33 for contacting and compressing the wings of the nose, acting as the rubber plates in the nose shape adjusting instrument according to the first preferred embodiment. The first and second body are preferably formed with synthetic resins which are safe to the skin.

Figure 11:
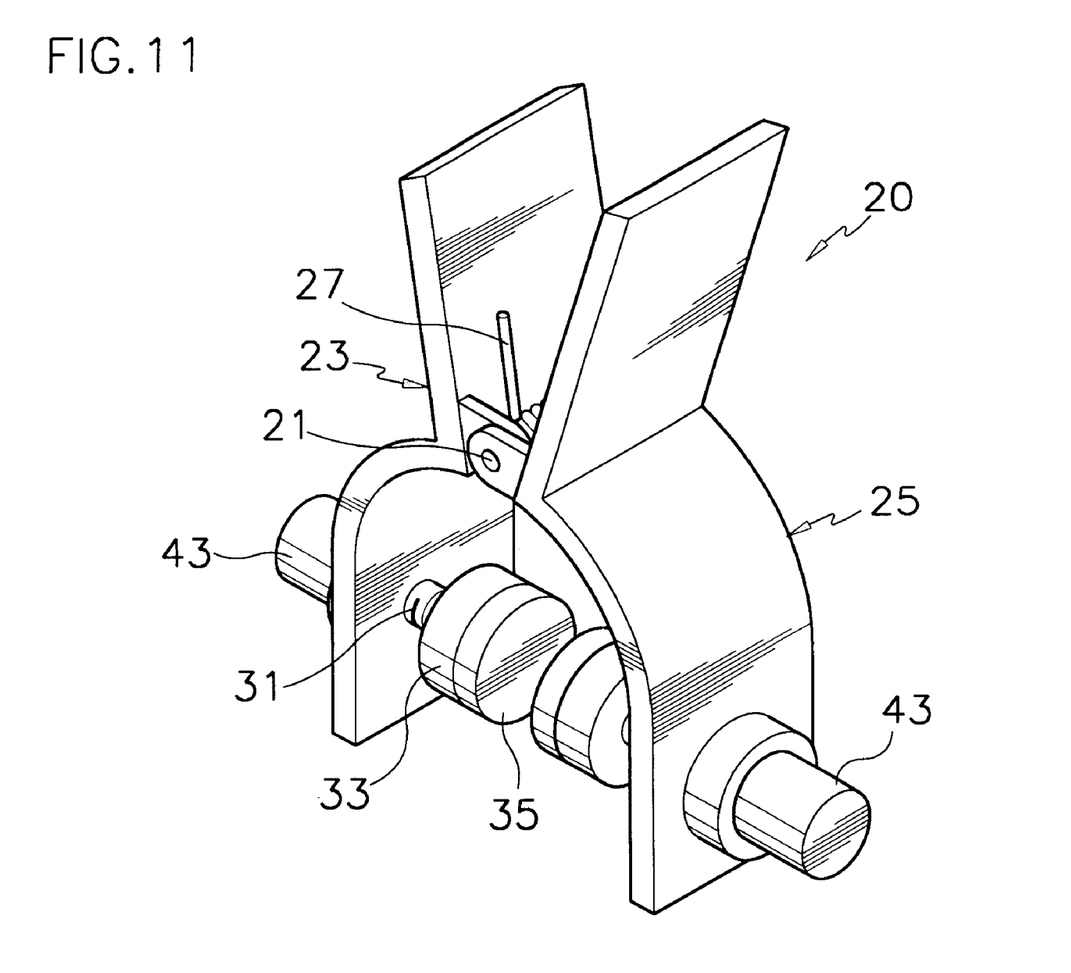
FIG. 11 is a schematic view of the nose shape adjusting instrument shown in FIG. 10 in a state where the bolt and the nut are tightened.

How this invented instrument is worn and operates is described hereinafter. First, the user presses the upper portions of the first and second body 23 and 25 such that the lowest ends of the first and the second body expand the distance therebetween. The user fits the wings of his or her nose between the contact plates 35 attached on the lower portions of the first and the second body 23 and 25. After fitting the nose between the contact plates 35, the user releases the pressure on the upper portions of the two bodies 23, 25. Then, the lowest ends of the first and the second body recover their original distance due to the elastic member 27 and consequently, his or her nose is slightly compressed between the contact plates 35. Thereafter, the user turns the adjusting bolts 31 to drive the same into the first and the second body (see FIG. 11), which will make the contact plates 35 attached on the supporting discs 33 more tightly compress the wings of the nose and elevate the tip of the nose.

Other embodiments of the invention will be apparent to the skilled in the art from consideration of the specification and practice of the invention disclosed herein. It is intended that the specification and examples be considered as exemplary only, with the true scope and spirit of the invention being indicated by the following claims.

What is claimed is:

1. A nose shape adjusting instrument comprising:
   a unitary inverted U-shaped body conforming to the general shape of a nose and having compressing portions on ends thereof opposite from a closed end of the body; the closed end of the body being shaped to comfortably engage the bridge of a wearer's nose;
   an attachment plate attached to each of the compressing portions;

a tightening bolt inserted through holes formed on the compressing portions for adjusting the distance between the compressing portions; and a tightening nut received on the tightening bolt for adjusting the spacing between the compressing portions.

2. A nose shape adjusting instrument according to claim 1, wherein a circular plate made of synthetic resins is attached on each of the attachment plates.

3. A nose shape adjusting instrument comprising:

a first body and a second body which are rotatably connected to each other by a hinge mechanism between upper portions and lower portions, the upper portions thereof forming a substantially V-shape and the lower portions forming an arch;

an elastic member acting between the first body and the second body, the elastic member exerting a biasing force urging the lower portions of the first body and the second body toward each other;

a first adjusting bolt threaded through the lower portion of the first body and a second adjusting bolt threaded through the lower portion of the second body, and first and second contact plates made of a resilient and soft material including silicon carried by the respective first and second adjusting bolts between the lower portions of the first and second bodies.

4. A nose shape adjusting instrument according to claim 3 wherein protrusions are formed on the bodies, the protrusions having holes therethrough for receiving a hinge pin.

5. A nose shape adjusting instrument according to claim 3, wherein bolt-supporting members are formed on the lower portions of the first and the second bodies, each having an aperture therethrough for receiving the adjusting bolt.

* * * * *